United States Patent (10) Patent No.: US 8,585,608 B2
Csatár et al. (45) Date of Patent: Nov. 19, 2013

(54) FLOW METER FOR PULMONARY FUNCTION TESTS

(75) Inventors: László Csatár, Budapest (HU); Kornél Nagy, Biatorbágy (HU)

(73) Assignee: Piston Kft., Budapest (HU)

( * ) Notice: Subject to any disclaimer, the term of this patent is extended or adjusted under 35 U.S.C. 154(b) by 948 days.

(21) Appl. No.: 12/619,424

(22) Filed: Nov. 16, 2009

(65) Prior Publication Data

US 2010/0145212 A1 Jun. 10, 2010

(30) Foreign Application Priority Data

Nov. 17, 2008 (HU) .................................... 0800685

(51) Int. Cl.
*A61B 5/08* (2006.01)
*G01F 1/37* (2006.01)
(52) U.S. Cl.
USPC ........................................ 600/538; 73/861.52
(58) Field of Classification Search
USPC .............................. 600/538; 73/861.52, 861.66
See application file for complete search history.

(56) References Cited

U.S. PATENT DOCUMENTS

| | | | |
|---|---|---|---|
| 4,418,723 A * | 12/1983 | Koni et al. ........................ | 138/42 |
| 4,640,293 A * | 2/1987 | Garbe ............................ | 600/529 |
| 4,884,459 A * | 12/1989 | Beyazov et al. ............ | 73/861.52 |
| 5,038,773 A | 8/1991 | Norlien et al. | |
| 5,048,327 A | 9/1991 | Atwood | |
| 5,088,332 A * | 2/1992 | Merilainen et al. ......... | 73/861.65 |
| 5,450,760 A * | 9/1995 | Lew et al. ................... | 73/861.77 |
| 6,142,148 A * | 11/2000 | Weckstrom et al. ...... | 128/204.22 |
| 6,634,242 B2 | 10/2003 | Cha et al. | |
| 6,681,643 B2 * | 1/2004 | Heinonen ................... | 73/861.52 |
| 6,915,701 B1 * | 7/2005 | Tarler ............................. | 73/774 |

* cited by examiner

*Primary Examiner* — Navin Natnithithadha
*Assistant Examiner* — Eric Messersmith
(74) *Attorney, Agent, or Firm* — Jason D. Voight

(57) ABSTRACT

A flow metering device for pulmonary function tests. The device has a sensing element extending in a longitudinal direction and defining an inner volume and an adapter unit. The sensing element is a measuring tube with open ends, and a pressure difference inducer is arranged in the measuring tube between the open ends. The pressure difference inducer is in contact with the measuring tube, partially occupies the inner cross section thereof, and is formed by spoke arms joined in pairs in a single point. The spoke arms in a pair close a given angle with one another, and pressure offtake grooves are formed in the surfaces of the spoke arms perpendicular to the longitudinal direction of the measuring tube. Such pressure offtake grooves enable a radial averaging of pressure. The adapter unit is provided with pneumatic low-pass filters formed as integral parts thereof.

11 Claims, 2 Drawing Sheets

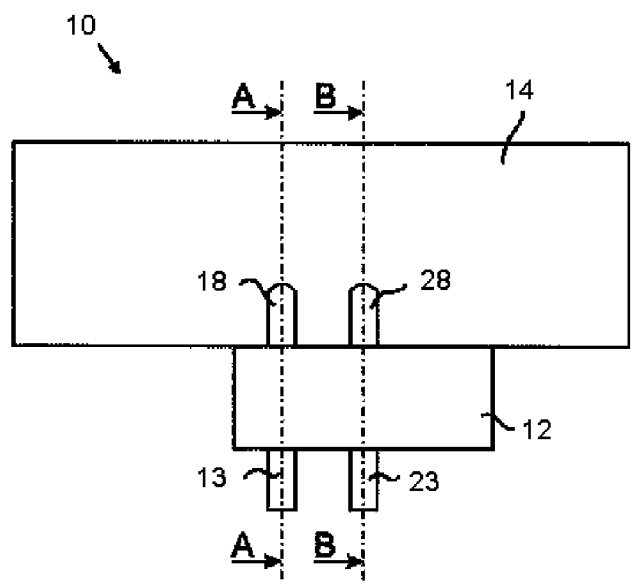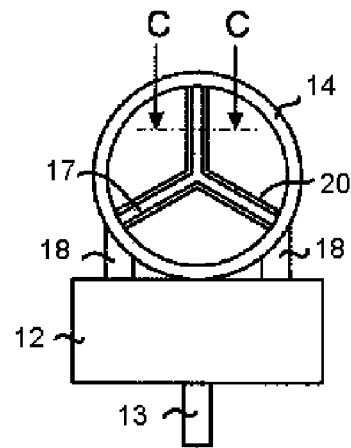
Figure 1A
Figure 1B
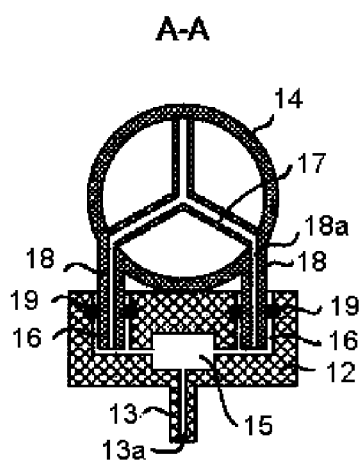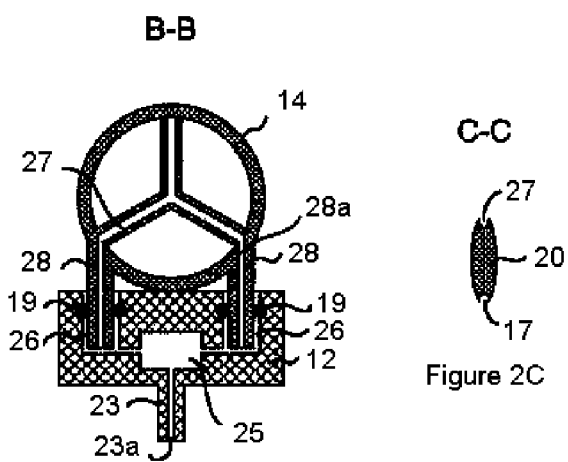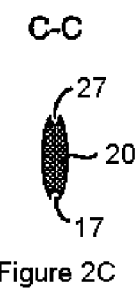
Figure 2A
Figure 2B
Figure 2C

FLOW METER FOR PULMONARY FUNCTION TESTS

REFERENCE TO RELATED APPLICATION

This is a regular U.S. patent application claiming priority of earlier Hungarian patent application no. P0800685, filed on Nov. 17, 2008, and entitled "Légzésdiagnosztikai áramlásmérő eszköz".

BACKGROUND OF THE INVENTION

1. Field of the Invention

The invention relates to a flow meter for pulmonary function tests, in particular to a Pitot tube flow metering device for pulmonary function tests.

2. Background Art

In everyday life, a great number of apparatuses for pulmonary function tests based on various operation principles facilitate the work of physicians in recognizing organic changes and/or defects of respiratory tracts, and/or when testing and monitoring respiratory functions. A class of apparatuses for pulmonary function tests is constituted by devices of direct construction (e.g. spirometers, rhinomanometers, whole body plethysmographs, diffusing capacity meters, ergospirometers) that involve a flow meter as the primary measuring transducer. Various means/techniques, such as e.g. means and processes based on the detection of change in ultrasonic waves or equipments and techniques based on the pressure difference measurements in various geometrical arrangements (i.e. employing different flow resistances) are made use of as the flow meter and/or to meter the air stream (induced, in general, by the respiration of the individual examined) flowing through the apparatus.

The Pitot or Prandtl tube equipments used to determine the difference between the static and stagnation pressures induced by an air stream are, in particular, based on a pressure difference measurement. The essence of such an equipment is that a double-wall probe is arranged, generally, within the measuring tube, by means of which the static and stagnation pressures created by the flow stream can be simultaneously measured. Then, based on Bernoulli's law, the magnitude of the unknown flow rate can be unambiguously determined. As the general advantage of the Pitot or Prandtl tube equipments, their relatively simple construction, small dead space and low flow resistance can be mentioned. Their great disadvantages are, however, that the useful signal generated by them is relatively noisy (i.e. in this case the signal-to-noise ratio influencing the precision and reliability of the measurement is not satisfactory) and/or their characteristics is nonlinear (quadratic).

U.S. Pat. No. 5,088,322 discloses an averaging Pitot tube flow measuring device for the measurement of a gas flow, in particular, a gas flow emerging due to exhalation/inhalation. Pressure lead-out elements of the Pitot tube are made in the form of radial pressure offtake vanes at the angle of 120° to one another. The surface of said vanes which is in contact with the gas flowing through the measuring tube is provided with channels suitable for leading away stagnation pressure. The channels extend along the full length of each vane, specifically from the inner surface of the wall of the measuring tube to an aperture located on the longitudinal axis of said measuring tube. Accordingly, for a certain vane, the averaging of pressure values takes place radially from the center of the measuring tube to the wall thereof. The arrangement of said vanes in which they are at the angle of 120° to one another enables the averaging of pressure values along the directions X and Y as well (here and from now on, direction Z corresponds to the direction parallel with the longitudinal axis of the measuring tube). Transmission of the pressure signal to a transducer arranged outside of the measuring tube takes place through said central aperture. In one of the embodiments, the vane surfaces provided with channels are located in a plane perpendicular to the longitudinal axis of the measuring tube. In a possible further embodiment, the vane surfaces extending from the inner surface of the measuring tube to the axis of symmetry thereof incline in the radial direction. A flow meter according to U.S. Pat. No. 5,088,332 is apt for measuring flow rates of either direction (i.e. in case of either exhalation or inhalation; symmetric construction). Said flow meter can also be used to analyze the gas composition flowing through the measuring tube. An outlet for the analysis of the gas composition is located symmetrically with respect to the central pressure offtake aperture, that is the measurement of both the pressure and the gas composition can be performed under the same conditions even if the flowing is of opposite direction.

The major disadvantage of said flow meter is that the pressure offtake aperture is located just at the geometrical center of the measuring tube, wherein the flow rate is the highest. Consequently, the risk of being contaminated by the minute moisture and/or the drops of sputum exhaled with air through getting into the offtake aperture is also the highest just at this point. As the flow meter at issue was primarily developed to monitor air breathing apparatuses, an appropriate filtering member is always incorporated into the total respiratory circuit when it is actually used for this purpose. However, in such an arrangement, the flow meter according to U.S. Pat. No. 5,088,332 is suitable for pulmonary function tests only in a limited manner. To avoid contamination through moisture and sputum, a surface coating capable of adsorbing water is optionally applied onto the vanes. When the flow meter is manufactured, this always means at least one further production step to be performed. This, as well as the coating applied itself increase the production costs of said flow meter. Moreover, the coating used encumbers significantly the recycling of the contaminated measuring tube.

International Publication Pamphlet No. WO 03/047429 teaches a symmetric and averaging Pitot tube respiratory flow metering device, as well as various pressure averaging techniques. Here, the Pitot tube is realized with a sensing tube arranged within a measuring tube, wherein said sensing tube is perpendicular to the direction of flow and crosses the longitudinal axis of said flow metering device. Sampling of pressure takes place through sensing bores formed on the sensing tube at its given points along the direction of the radius of the measuring tube. A disadvantage of said flow metering device is that it is apt for averaging only along one of the directions X and Y at a time. Another disadvantage of the device at issue is that the sensing tube cannot be removed together with the measuring tube after every single measurement and, hence, there is a possibility of cross infection between individuals examined one after the other if disinfection of said device is inappropriate. A further disadvantage of the flow metering device concerned is that the sensing bores used for the sampling get easily clogged (because of their sizes) due to the moisture and/or sputum content of the exhaled air. This holds especially for diagnostic inspections of the lung.

The flow meter head according to Polish Patent No. 173,767 also represents essentially a symmetric and averaging Pitot tube flow metering device. A disadvantage of said device is that the aerodynamical resistance forming a part thereof only measures a vertical segment of the flow traveling through the measuring tube, that is, it averages only along a single direction. Another disadvantage of the device concerned is that the channels within said resistance directly guide the moisture/sputum condensing within the measuring tube into the pressure gauge sensing means.

U.S. Pat. No. 5,038,773 discloses a further symmetric and averaging Pitot tube flow metering device that is basically made use of as a disposable flow meter. In this device, bores for pressure sampling are formed in the ends of two ribs located in the vicinity of the inner surface of the measuring tube wherein said ribs are crossing each other and arranged in the path of flow within said measuring tube. As a consequence—and accordant to the above—the risk of being contaminated decreases, since at the positions of the sampling bores the velocity of an air stream flowing through the measuring tube becomes smaller. In turn, when said flow meter is to be used for pulmonary function tests, said bores can easily be clogged by the moisture and/or sputum content of the exhaled air due to their small cross sections. A further disadvantage of said flow metering device is that the pressure sensing bores formed in the vicinity of the ends of the ribs do not enable radial averaging.

As it has been mentioned earlier, a common disadvantage of the Pitot tube flow metering devices is that their signal-to-noise ratios are dissatisfactory and should be enhanced in most cases. In Pitot tube measuring techniques and flow meters the enhancement of the signal-to-noise ratio is performed on electric signals obtained by transducers and corresponding to the pressure signals by either electronic circuits representing a low-pass filter or by means of appropriate softwares. Increase in the signal-to-noise ratio takes place, in general, relatively far away from the place where the pressure signals were actually generated, and thus said pressure signals can be further distorted during their propagation. As a consequence of this, the precision and dynamics of the measurement degrades.

U.S. Pat. No. 5,048,327 teaches a Venturi tube gas flow metering device to be used for governing the fuel injection system of internal combustion engines, wherein the signal-to-noise ratio of the difference signal of a high pressure and a low pressure is increased by means of a low-pass pneumatic filtering arrangement. To this end, before the operation of comparison, said high pressure is guided through a conduit representing a flow resistance R and a ring-shaped reservoir representing a capacitance C, filtering out the pressure fluctuations present in the high pressure thereby. Said U.S. patent is expressedly limited to Venturi tube flow meters, the applicability of a low-pass pneumatic filtering arrangement in other type of flow meters is not mentioned (and is not even hinted at). Furthermore, said document contains no teaching as to the adaptation of said filtering arrangement for flow meters based on other principles.

SUMMARY OF THE INVENTION

In light of the above, the aim of the present invention is to provide a flow metering device eliminating or at least reducing the disadvantages of the Pitot tube flow meters discussed.

In particular, the present invention aims at providing a Pitot tube flow metering device for pulmonary function tests that is of a simple construction, compact and optionally also disposable, and which is capable of enhancing the signal-to-noise ratio of the measured pressure signals through the application of no electronic components, as well as in the vicinity of the place of generation of said pressure signals.

A yet further object of the present invention is to provide a flow metering device for pulmonary function tests that tends to get contaminated up to a smaller extent than the devices discussed earlier and at the same time it is also apt for an averaging along a radial direction in the flow cross section besides the averaging completed along the directions X and Y.

A yet further object of the present invention is to provide a flow metering device of small dead space for pulmonary function tests that provides a precise flow metering with low flow resistance in a broad range of flow and along with a low risk of cross infection.

A yet further object of the present invention is to manufacture a flow metering device that can optionally be recycled in a simple and cost effective manner.

The objects aiming at the provision of the flow metering device for pulmonary function tests according to the invention are achieved by providing a flow metering device according to claim 1. Possible further preferred embodiments of said flow metering device for pulmonary function tests according to the invention are set forth in Claims 2 to 6.

BRIEF DESCRIPTION OF THE DRAWINGS

In what follows, the invention is discussed in more detail with reference to the attached drawing, wherein FIG. 1A illustrates a possible embodiment of the Pitot tube flow metering device for pulmonary function tests in accordance with the invention in side view;

FIG. 1B is a front view of the flow metering device for pulmonary function tests shown in FIG. 1A;

FIGS. 2A and 2B are sectional views along A-A and B-B, respectively, through the flow metering device for pulmonary function tests illustrated in FIG. 1A;

FIG. 2C is a sectional view along C-C through one of the arms of the pressure offtake element used in the flow metering device for pulmonary function tests shown in FIG. 1B;

Figure 3A:
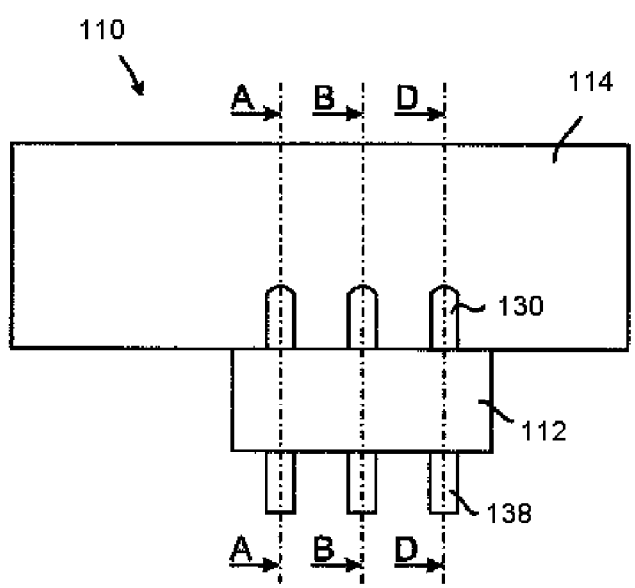
FIG. 3A illustrates a further possible embodiment of the Pitot tube flow metering device for pulmonary function tests in accordance with the invention in side view, said embodiment is also provided with a sampling offtake.

It is hereby noted that in the drawing, similar reference signals refer to similar or identical structural elements.

DETAILED DESCRIPTION OF THE PREFERRED EMBODIMENTS

FIGS. 1 and 2 illustrate a possible embodiment 10 of the flow metering device according to the invention in various views. The flow metering device 10 comprises a pneumatic adapter unit 12 and a measuring tube 14 connectable to the adapter unit 12 by a single movement in a detachable, but pressure tight manner. Said detachable connection forms by inserting pressure signal offtake stubs 18, 28 with channels 18a, 28a, respectively, of the measuring tube 14 into reception bores 16, 26 formed in said adapter unit 12. The pressure tight closure is accomplished by sealing members 19, provided preferably in the form of O-rings, placed preferably in said reception bores 16, 26. When a measurement takes place, a patient gets into contact merely with the measuring tube 14. After completion of the measurement, due to this construction, the measuring tube 14 of the flow metering device 10 can simply and rapidly be disconnected from the adapter unit 12 and replaced by a further (e.g. sterile) measuring tube. The measuring tube 14 detached in this way might be prepared for a subsequent usage by means of sterilizing or can simply be destroyed as dangerous waste. In this way, the flow metering device according to the invention ensures prevention of both the cross infections between patients and the device getting infectious (and/or contaminated).

The flow metering device 10 for pulmonary function tests according to the invention is basically a symmetric and averaging Pitot tube device. A spoke 20 forming a pressure offtake element is arranged within the measuring tube 14 of given length, essentially at about the half of said length. In the shown embodiment, said spoke 20 is formed by three spoke arms that are essentially perpendicular to the longitudinal axis of the measuring tube 14 and extend radially to the inner surface of the wall of said measuring tube 14. To decrease (to minimize) the flow resistance, each spoke arm is of an approximate guttiform in cross section. In this embodiment, the spoke arms are equal in length and join at the angle of 120° to one another in such a way that said spoke 20 is symmetric with respect to a plane that is incident to the longitudinal axis of the measuring tube 14 and parallel with the geometrical axes of said reception bores 16, 26. As is apparent to a person skilled in the art, the spoke 20 can also be realized with different geometries, e.g. with more than three spoke arms, with different angles of join of the spoke arms or with various lengths of the spoke arms, and/or tilted in a small angle (preferably of at most 15°) relative to a plane perpendicular to the longitudinal axis of the measuring tube 14 (i.e. to the direction of flow). A requisite for suitable geometries is that the flow metering device 10 should remain apt for averaging along both independent directions in the plane perpendicular to the flow direction and, furthermore, the flow resistance should be kept at a relatively low value.

The spoke 20 is of a given length along the direction of flow. As it is shown in FIGS. 2A and 2B, pressure offtake grooves 17, 27 are formed in the end surfaces of said spoke 20 that are perpendicular to the direction of flow. The grooves 17, 27 start at the joint of the spoke arms, extend along each spoke arm and the spoke arms located symmetrically with respect to said plane of symmetry connect into respective through holes formed in the wall of the measuring tube 14 and thus open into the channels 18a, 28a of the pressure signal offtake stubs 18, 28. The grooves 17, 27 formed in the end surfaces of the third spoke arm, which is incident to said plane of symmetry, terminate at the inner surface of the wall of the measuring tube 14; no pressure signal offtake stubs are connected to them. The pressure offtake grooves 17, 27 correspond to the double-wall probe of a Pitot tube, play its part in a measurement, i.e. they lead away the pressure signals averaged both along the independent directions in a plane perpendicular to the direction of flow and radially from the measuring tube 14 at extreme points, that is through the wall of said measuring tube 14. As the pressure offtake grooves 17, 27 start at the middle of the measuring tube 14 and extend to the wall thereof, said grooves perform the radial averaging for the full cross section of the flow. The through holes receiving the pressure offtake grooves 17, 27 are formed in the wall of the measuring tube in a position so as to locate slightly higher than the lowest point of the measuring tube 14. In the embodiments of the flow metering device 10 illustrated in FIGS. 1 and 2, said through holes are formed in the wall of the measuring tube 14 at such a height that the grooves 17, 27 close the angles of essentially 60° with the channels 18a, 28a. According to the studies performed, the risk of inflowing of the condensing moisture and/or the secretion/sputum carried by the exhaled air stream into said adapter unit 12 and thereby its contamination can be eliminated or at least significantly decreased with a construction of this type.

When the measuring tube 14 becomes connected to the adapter unit 12, said channels 18a, 28a of the pressure signal offtake stubs 18, 28 open into pneumatic low-pass filters 15, 25, respectively. Each filter 15, 25 consists of two constrictions, i.e. two resistances in series, and a cavity of a relatively large volume formed within the adapter unit 12, i.e. a capacitive member in parallel. When a measurement takes place, said filters 15, 25 filter the noisy pressure difference signal generated by the pressure offtake grooves 17, 27, as Pitot tubes, and transmitted via the channels 18a, 28a of the pressure signal offtake stubs 18, 28 and thus increase the signal-to-noise ratio thereof. Said filtering serves for eliminating portions of the pressure signals (i.e. the fluctuations) with frequencies higher than a given (so-called cutoff) frequency. The cut-off frequency is set by the volume ratio of said constrictions and said cavity when the adapter unit 12 is fabricated. By forming constrictions and a cavity leading to various volume ratios, adapter units 12 operating at different cut-off frequencies can be prepared. Moreover, as the pressure signal offtake stubs 18, 28 are relatively short in length, filtering of the useful signal takes place essentially at the place of generation of said signal. Thus, the precision and the dynamics of the pressure difference measurement is basically preserved.

The pneumatic low-pass filters 15, 25 are connected to the channels 13a, 23a of output pressure signal offtake stubs 13, 23 that serve for transmitting the filtered pressure difference signal to a transducer (not shown in the drawing), preferentially to a differential pressure-gauge.

Figure 3B:
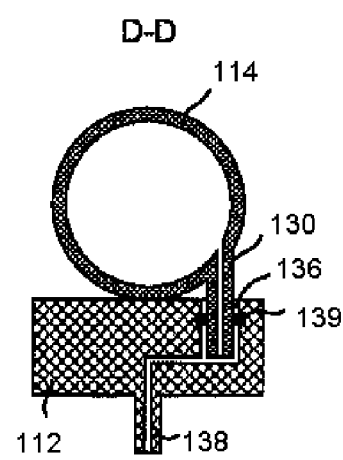
FIG. 3B is a sectional view along D-D through the flow metering device for pulmonary function tests illustrated in FIG. 3A.

FIGS. 3A and 3B illustrate a possible further embodiment 110 of the flow metering device according to the invention. As to the measuring of pressure difference, this embodiment is identical to the one discussed with reference to FIGS. 1 and 2. Thus, in what follows, the identical structural parts and their functions are not discussed in detail. A flow metering device 110 differs from the flow metering device 10 in that its measuring tube 114 is provided with at least one further gas sampling connecting stub 130 in communication with the inner volume of the measuring tube 114, while its adapter unit 112 is provided with a reception bore 136 receiving said connecting stub 130 in a detachable, but pressure tight manner, as well as a sample offtake stub 138 for transporting the sample taken out from the measuring tube 114 into a suitable analyzing means (not shown in the drawing). The pressure tight closure is accomplished by a sealing member 139, also provided preferably in the form of an O-ring, placed preferably into said reception bore 136. In this embodiment, the gas sampling connecting stub 130 also joins to the measuring tube 114 at an angle of 60°, i.e. at a location that forms not the lowest point of said measuring tube 114. According to the studies performed, the risk of inflowing of the condensing moisture and/or the secretion/sputum carried by the exhaled air stream into said adapter unit 112 and thereby its contamination can be eliminated or at least significantly decreased with a construction of this type.

By making use of said gas sampling connecting stub 130, the flow metering device 110 for pulmonary function tests according to the invention is also suitable for performing extended pulmonary function tests. Such an extended pulmonary function testing technique is e.g. the diffusing capacity measurement or ergospirometry wherein there is also a need to determine the gas composition of the exhaled and inhaled air.

In view of the above teaching, it is apparent that the compact Pitot tube flow metering device for pulmonary function tests according to the invention ensures a precise flow metering with low flow resistance in a wide range of flow. The risk of cross infection is low due to the fact that said measuring tube can simply be detached from the adapter unit and hence replaced.

Furthermore, by means of applying (tuned) pneumatic filters integrated with the adapter unit, the flow metering device for pulmonary function tests according to the invention eliminates one of the major disadvantages of Pitot tube flow meters according to which the difference pressure signal is very noisy. Due to the inclusion of pneumatic filters, in this case there is basically no need to increase the signal-to-noise ratio electronically.

The flow metering device for pulmonary function tests according to the invention is cheap and enables a large scale mass production, making it ideally suited even to use as disposable medical device. Moreover, as both the measuring tube and the adapter unit can optionally be made of a single material (preferentially, by means of e.g. injection molding of a suitable plastic material), in lack of possibility and/or objective to sterilize the measuring tube, an already spent flow meter can simply be recycled to the full extent, thereby decreasing significantly the manufacturing and recycling costs of such type of devices.

Although the present invention has been described in detail for the purpose of illustration, various variations and modifications of the invention as disclosed, in addition to those described herein, will become apparent to those of skill in the art from the foregoing description. Such variations and modifications are intended to be encompassed within the scope of the present claims.

What is claimed is:

1. A flow metering device for pulmonary function tests, comprising a sensing element extending in a longitudinal direction and defining an inner volume and an adapter unit, wherein said sensing element is a measuring tube with open ends, and wherein a pressure difference inducing means is arranged in the measuring tube between the open ends, said pressure difference inducing means comprises surfaces perpendicular to the longitudinal direction of the measuring tube, is in contact with the measuring tube and partially occupies its inner cross section, said pressure difference inducing means is formed by spoke arms in pairs joined in a single point, the spoke arms in a pair close a given angle with one another, and pressure offtake grooves are formed in the surfaces perpendicular to the longitudinal direction of the measuring tube of said spoke arms, wherein the pressure offtake grooves start at a point of join of the spoke arms and at least some of the grooves open into respective through holes formed in the measuring tube so as to provide radial averaging for the full inner cross section of the measuring tube, the measuring tube is provided on its outer side with pressure signal offtake stubs, each stub having an internal channel, wherein each of said channels of said pressure signal offtake stubs is in communication with the inner volume of the measuring tube via one of said through holes, and the adapter unit is provided with reception bores capable of receiving the pressure signal offtake stubs in a detachable and pressure tight manner, said reception bores are in communication with pressure signal offtake stubs of the adapter unit and each reception bore forms a continuous flow path with the respective channel of the pressure signal offtake stub received thereby when the measuring tube becomes connected with the adapter unit, and pneumatic low-pass filters formed as integral parts of the adapter unit are incorporated in between said reception bores and said pressure signal offtake stubs of the adapter unit so as to ensure filtering out fluctuations of the pressure signals led away from the inner volume of said measuring tube separately by means of the pressure offtake grooves located in opposite surfaces of said spoke arms.

2. The flow metering device of claim 1, wherein each pneumatic low-pass filter is formed as an ensemble of constrictions and a cavity connected to said constrictions formed within the bulk of the adapter unit, wherein a cut-off frequency for said fluctuations is determined by the volume ratio of the constrictions and the cavity.

3. The flow metering device of claim 1, wherein the number of spoke arms is three and the spoke arms are arranged symmetrically with respect to a plane that is incident to the longitudinal axis of the measuring tube and parallel with the geometrical axes of the reception bores.

4. The flow metering device of claim 3, wherein the angle of join is 120° for each pair of spoke arms, said spoke arms are equal in length and said through holes are formed in the measuring tube at those ends of the symmetrically located spoke arms which locate at said measuring tube.

5. The flow metering device of claim 1, wherein the measuring tube comprises a gas sampling connecting stub in communication with the inner volume of said measuring tube, the adapter unit comprises a reception bore capable of receiving said gas sampling connecting stub in a detachable and pressure tight manner, said reception bore is in communication with a sample offtake stub of the adapter unit, wherein the gas sampling connecting stub, the reception bore and the sample offtake stub form a continuous flow path when said measuring tube and said adapter unit becomes connected.

6. The flow metering device of claim 1, wherein said pressure tight manner is achieved by sealing members arranged between respective elements fitted into one another when said measuring tube is connected with said adapter tube.

7. The flow metering device of claim 2, wherein the number of spoke arms is three and the spoke arms are arranged symmetrically with respect to a plane that is incident to the longitudinal axis of the measuring tube and parallel with the geometrical axes of the reception bores.

8. The flow metering device of claim 7, wherein the angle of join is 120° for each pair of spoke arms, said spoke arms are equal in length and said through holes are formed in the measuring tube at those ends of the symmetrically located spoke arms which locate at said measuring tube.

9. The flow metering device of claim 4, wherein the measuring tube comprises a gas sampling connecting stub in communication with the inner volume of said measuring tube, the adapter unit comprises a reception bore capable of receiving said gas sampling connecting stub in a detachable and pressure tight manner, said reception bore is in communication with a sample offtake stub of the adapter unit, wherein the gas sampling connecting stub, the reception bore and the sample offtake stub form a continuous flow path when said measuring tube and said adapter unit becomes connected.

10. The flow metering device of claim 9, wherein said pressure tight manner is achieved by sealing members arranged between respective elements fitted into one another when said measuring tube is connected with said adapter tube.

11. A flow metering device for pulmonary function tests, consisting of a sensing element extending in a longitudinal direction and defining an inner volume and an adapter unit, wherein said sensing element is a measuring tube with open ends, and wherein a pressure difference inducing means is arranged in the measuring tube between the open ends, said pressure difference inducing means comprises surfaces perpendicular to the longitudinal direction of the measuring tube, is in contact with the measuring tube and partially occupies its inner cross section, said pressure difference inducing means is formed by three spoke arms in pairs joined in a single point, the spoke arms in a pair close a given angle with one another, and pressure offtake grooves are formed in the surfaces perpendicular to the longitudinal direction of the measuring tube of said spoke arms, wherein the pressure offtake grooves start at a point of join of the spoke arms and at least some of the grooves open into respective through holes formed in the measuring tube so as to provide radial averaging for the full inner cross section of the measuring tube, the measuring tube is provided on its outer side with pressure signal offtake stubs, each stub having an internal channel, wherein each of said channels of said pressure signal offtake stubs is in communication with the inner volume of the measuring tube via one of said through holes, and the adapter unit is provided with reception bores capable of receiving the pressure signal offtake stubs in a detachable and pressure tight manner, said reception bores are in communication with pressure signal offtake stubs of the adapter unit and each reception bore forms a continuous flow path with the respective channel of the pressure signal offtake stub received thereby when the measuring tube becomes connected with the adapter unit, and said spoke arms are arranged symmetrically with respect to a plane that is incident to the longitudinal axis of the measuring tube and parallel with the geometrical axes of the reception bores, and pneumatic low-pass filters formed as integral parts of the adapter unit are incorporated in between said reception bores and said pressure signal offtake stubs of the adapter unit so as to ensure filtering out fluctuations of the pressure signals led away from the inner volume of said measuring tube separately by means of the pressure offtake grooves located in opposite surfaces of said spoke arms.

* * * * *